United States Patent [19]

Crisafulli et al.

[11] Patent Number: 4,602,015

[45] Date of Patent: Jul. 22, 1986

[54] 2-PIPERAZINOPYRIMIDINE SALT AND PHARMACEUTICAL COMPOSITIONS CONTAINING IT

[75] Inventors: Emilio Crisafulli, Milan; Marco Frigerio, Mantova, both of Italy; Jean-Paul Kan, Clapiers, France

[73] Assignee: Sanofi, Paris, France

[21] Appl. No.: 709,691

[22] PCT Filed: Jun. 21, 1984

[86] PCT No.: PCT/FR84/00156

§ 371 Date: Feb. 14, 1985

§ 102(e) Date: Feb. 14, 1985

[87] PCT Pub. No.: WO85/00168

PCT Pub. Date: Jan. 17, 1985

[30] Foreign Application Priority Data

Jun. 24, 1983 [FR] France .................................. 83 10525

[51] Int. Cl.⁴ .................. A61K 31/495; C07D 403/04

[52] U.S. Cl. ..................................... 514/252; 544/295

[58] Field of Search ......................... 544/295; 514/252

[56] References Cited

U.S. PATENT DOCUMENTS

| | | | |
|---|---|---|---|
| 2,472,583 | 6/1949 | Gzemski .............................. | 546/139 |
| 2,606,906 | 4/1952 | Hultquist et al. ................... | 544/295 |
| 2,748,125 | 5/1956 | Hofmann ............................. | 544/295 |
| 2,748,129 | 5/1956 | Hofmann ............................. | 544/295 |

Primary Examiner—Glennon H. Hollrah
Assistant Examiner—James H. Turnipseed
Attorney, Agent, or Firm—Stevens, Davis, Miller & Mosher

[57] ABSTRACT

A salt of 2-(1-piperazinyl) pyrimidine salt with 2-naphthalene sulfonic acid, having a dopaminergic psychotropic activity and pharmaceutical compositions containing it as active principle for the treatment of behavioral problems.

4 Claims, No Drawings

2-PIPERAZINOPYRIMIDINE SALT AND PHARMACEUTICAL COMPOSITIONS CONTAINING IT

The present invention relates to a novel salt of 2-piperazinopyrimidine having a dopaminergic psychotropic action.

More particularly, the present invention concerns the 2-(1-piperazinyl)pyrimidine 2-naphtalenesulfonate, a process for its preparation and pharmaceutical compositions containing it as active ingredient.

The 2-(1-piperazinyl)pyrimidine, in the form of free base, is a compound well known in literature; it is used as a synthesis intermediate.

It has been tested among a number of compounds none of which has shown analgesic or antifilarial activity (H. W. Stewart et al., J. Org. Chem. 1953, 18, 1478–1483).

This compound has been isolated as an active metabolite of the anxiolytic agent buspirone (J. Chromatography 1982, 252, 310–314).

It has now been found that the 2-(1-piperazinyl)pyrimidine 2-naphtalenesulfonate possesses a very good psychotropic activity with dopaminergic mechanism of action, particularly antipsychotic, antidepressive and tranquillizing-sedative activity.

It has also surprisingly been found that the salt of 2-(1-piperazinyl)pyrimidine with 2-naphtalenesulfonic acid is much more active, in the absolute sense, than both the corresponding free base and the hydrochloride thereof and that its very high activity is long-lasting and increases with time.

Thus, it is an object of the present invention, to provide the salt of 2-(1-piperazinyl)pyrimidine with 2-naphtalenesulfonic acid of formula

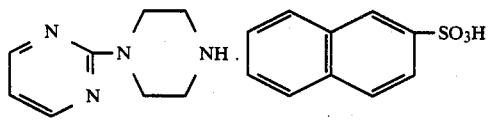

I hereinafter designated "2-(1-piperazinyl)pyrimidine napsilate".

The compound of the present invention is prepared according to another aspect of the present invention by a process of salification, characterised in that 2-(1-piperazinyl)-pyrimidine is treated with an equimolecular amount of 2-naphtalenesulfonic acid in an organic or aqueous organic solvent.

An alcohol, such as isopropanol, acetone or the like is preferably used as organic solvent.

The salt thus obtained is isolated according to conventional procedures by simple filtration and, if necessary, by crystallisation.

The salification may be carried out on the crude 2-(1-piperazinyl)pyrimidine as obtained from the reaction of 2-chloropyrimidine and piperazine according to known procedures.

According to a preferred mode operandi, the starting 2-(1-piperazinyl)pyrimidine is used in the form of hydrochloride and the 2-naphtalenesulfonic acid is used in the form of an alkaline salt, preferably sodium salt. Salification occurs at temperature of from 50° to 70° C. in an aqueous organic solvent, such as acetone, containing from 5 to 20% of water.

The antidepressive activity of the compound of the invention has been evaluated in the test of antagonism of prochlorperazine-induced catalepsy (K. Biziere et al., Arzneimittel Forschung, 1982, 32 (II), 824–831). The 2-(1-piperazinyl)pyrimidine napsilate and the corresponding free base, as reference compound, were administered orally to groups of 10 Wistar male rats weighing 220–240 g; at the same time control animals were treated with saline. One hour later, prochlorperazine was administered subcutaneously at a dose of 10 mg/kg. Five hours after this administration, the number of cataleptic animals was assessed by the cork test. According to this test the animals were placed with their forepaws on a stand formed by three superposed corks (11 cm total height) and forced to maintain this position for 20 seconds at least. The performances of each group of animals were compared with those of the controls having received the vehicle and prochlorperazine only.

Table I hereinbelow shows the ED50 of the tested compounds.

TABLE I

| Compound | Prochlorperazine Catal. antag. $ED_{50}$ mcmol/kg |
|---|---|
| 2-(1-piperazinyl)-pyrimidine napsilate | 5.7 (5.0–6.4) |
| 2-(1-piperazinyl)-pyrimidine base | 24 (12–45) |

It results from this table that the 2-(1-piperazinyl)pyrimidine napsilate of the present invention is about 4 times more active orally than the corresponding free base in the test of prochlorperazine-induced catalepsy, predictive of antidepressive activity.

The dopaminergic mechanism of the compound of the invention was studied in comparison with the corresponding free base and its hydrochloride by analysing the rotational behaviour in mice after unilateral lesion of the striatum (P. Protais et al., J. Pharmacol. 1976, 7, 251–255).

Female Charles River CD1 mice weighing 20–24 g were previously subjected to a unilateral lesion of the striatum by stereotaxic injection of 8 mcg/animal of 6-hydroxydopamine. A week later, the 2-(1-piperazinyl)-pyrimidine napsilate, the 2-(1-piperazinyl)-pyrimidine hydrochloride and the free base were administered by oral route to groups of six mice at a dose corresponding to 0.15 mg/kg of free base. The number of turns was recorded, during 2 minutes, one hour after the administration of the three products. The turns ipsilateral to the lesion were plotted as positive values, the contralateral turns were plotted as negative values. The algebric sum of turns for each group of treated animals was compared to that of control animals treated with the vehicle (saline) only.

Table II hereinbelow shows the percent variation of turns, as compared to the controls.

TABLE II

| Compound | Dose (mg/kg) | Variation % |
|---|---|---|
| 2-(1-piperazinyl)-pyrimidine base | 0.15 | −94** |
| 2-(1-piperazinyl)pyrimidine hydrochloride | 0.18 | −29 ns |
| 2-(1-piperazinyl)pyri- | 0.34 | −117** |

TABLE II-continued

| Compound | Dose (mg/kg) | Variation % |
|---|---|---|
| midine napsilate | | |

**significant $p < 0.01$
ns: not significant
"t" Student test

It results from this table that the base significantly reduces the algebric sum of turns ipsilateral and contralateral to the lesion whilst the hydrochloride has no significant effect. Moreover, the napsilate not only reduces the above algebric sum, but it also shows a negative variation higher than 100%, which proves that the number of turns contralateral to the lesion is higher than the number of the ipsilateral turns. Thus, napsilate possesses a dopaminergic activity higher than that of the free base whereas hydrochloride is nearly inactive in these conditions.

The dopaminergic action of the compound of the present invention has also been evaluated in the time in comparison with the corresponding free base and the hydrochloride thereof. Table III hereinbelow shows the percent variations of the turns ipsilateral and contralateral to the lesion, 60, 180 and 360 minutes after the oral administration of the three products, at a dose corresponding to 0.15 mg/kg of free base, as compared to the controls having received the vehicle only.

TABLE III

| Compound | Variation % after minutes: | | |
|---|---|---|---|
| | 60 | 180 | 360 |
| 2-(1-piperazinyl)-pyrimidine base | −94** | −62** | −60** |
| 2-(1-piperazinyl)-pyrimidine hydrochloride | −29 ns | −28 ns | −22 ns |
| 2-(1-piperazinyl)-pyrimidine napsilate | −117** | −126** | −147** |

**significant $p < 0.01$
ns: not significant
"t" Student test

It results from this table that 2-(1-piperazinyl)-pyrimidine hydrochloride is inactive with the time too and that the activity of the free base tends to decrease with the time. On the contrary, the 2-(1-piperazinyl)pyrimidine napsilate of the present invention is more potent than the reference products and, in addition, its activity increases significantly with the time.

The dopaminergic psychotropic activity of the compound of the present invention and its low toxicity make it useful as a drug.

Thus, according to another of its aspects, the present invention concerns pharmaceutical compositions containing 2-(1-piperazinyl)pyrimidine napsilate as active ingredient.

In the pharmaceutical compositions of the present invention for oral, parenteral, sublingual, transdermic or rectal administration, the 2-(1-piperazinyl)pyrimidine napsilate utilized as active ingredient may be administered in dosage unit forms, in admixture with conventional pharmaceutical carriers to animals and human beings for the treatment of humour and behaviour disorders, more particularly in the management of psychosis, depression, as well as anxiety and insomnia. Appropriate dosage unit forms include forms for oral administration, such as tablets, capsules, powders, granules and oral solutions or suspensions and suppositories for rectal administration.

In order to obtain the desired psychotropic effect, the daily dose of active ingredient may vary between 0.1 and 100 mg per kg of body-weight and per day.

Each unit dose may contain from 1 to 300 mg of active ingredient in admixture with a pharmaceutical carrier. This unit dose may be administered from 1 to 4 times daily to treat the humour or behaviour disorders.

The following examples illustrate the invention without, however, limiting it.

EXAMPLE 1

To a solution of 3 g (0.015 mol) of 2-(1-piperazinyl)-pyrimidine hydrochloride in 12 ml of water, heated to 50°–60° C., there is added a solution of 3.44 g (0.015 mol) of sodium 2-naphtalenesulfonate in a mixture of 120 ml of acetone and 12 ml of water previously heated at the above-mentioned temperature. After cooling and filtration, 4.6 g (82%) of pure 2-(1-piperazinyl)pyrimidine napsilate are obtained; m.p. 218°–221° C. Analysis: total S: Calc. 8.61%; Found 8.51%.

The structure has been confirmed by the infra-red (IR) and ultraviolet (UV) spectra and the nuclear magnetic resonance (NMR).

EXAMPLE 2

A mixture of 3.2 g of 2-chloropyrimidine and 12.1 g of anhydrous piperazine in 100 ml of absolute ethanol is heated at reflux for 18 hours, then it is thoroughly evaporated under reduced pressure and in the warm. The residue is taken up with 400 ml of diethyl ether, the solution thus obtained is washed with 10 ml of an aqueous solution of sodium hydroxide 1:1, then with 20 ml of water. The organic solution is dried over anhydrous sodium sulfate, filtered and evaporated to dryness under reduced pressure. The oil thus obtained is dissolved in 30 ml of isopropanol and 4.38 g of 2-naphtalenesulfonic acid dissolved in 30 ml of isopropanol are added to the solution at about 60° C. From the solution thus obtained a product crystallizes which is filtered and dried to give 2-(1-piperazinyl)pyrimidine napsilate identical to the product of Example 1.

EXAMPLE 3

Capsules containing 2-(1-piperazinyl)pyrimidine napsilate having the following composition:

| active ingredient | 15 mg |
|---|---|
| lactose | 120 mg |
| magnesium stearate | 5 mg | are prepared by intimately mixing charges of the ingredients above and introducing the mixture into hard gelatine capsules.

EXAMPLE 4

Tablets comprising 2-(1-piperazinyl)pyrimidine napsilate, having the following composition:

| active ingredient | 20 mg |
|---|---|
| lactose | 100 mg |
| microcrystalline cellulose | 30 mg |
| dried corn starch | 40 mg |
| magnesium stearate | 5 mg | are prepared by crushing the active ingredient to a particle dimension of 0.4 mm size, by passing it through a 0.4 mm sieve, by mixing the crushed mixture with the other constituents and compressing to form the tablets.

In the same manner, tablets comprising 40 mg of active ingredient are prepared.

EXAMPLE 5

By operating as described in Example 4 hereinabove, tablets having the following composition are prepared:

| active ingredient | 50 mg |
|---|---|
| lactose | 95 mg |
| corn starch | 100 mg |
| talc | 4.5 mg |
| magnesium stearate | 0.5 mg |

EXAMPLE 6

Suppositories comprising 2-(1-piperazinyl)pyrimidine napsilate are prepared having the following composition:

| active ingredient | 50 mg |
|---|---|
| lactose | 250 mg |
| mass for suppositories | q.s.f. 1.7 g |

The active substance is mixed with the lactose and the mixture is placed in the molten mass for suppositories uniformly. The suspension is poured into cooled moulds to form suppositories weighing 1.7 g.

We claim:

1. The 2-(1-piperazinyl)pyrimidine 2-naphthalenesulfonate of formula

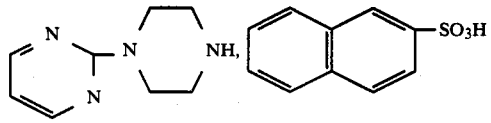

2. A pharmaceutical composition having dopaminergic psychotropic action containing, as active ingredient, the compound according to claim 1.

3. A pharmaceutical composition according to claim 2, which is in dosage unit form.

4. A pharmaceutical composition according to claim 3, characterised in that it contains from 1 to 300 mg of active ingredient per dosage unit in admixture with a pharmaceutical carrier.

* * * * *